(12) United States Patent
Zucker

(10) Patent No.: US 12,336,764 B2
(45) Date of Patent: Jun. 24, 2025

(54) SURGICAL PATH PLANNING USING ARTIFICIAL INTELLIGENCE FOR FEATURE DETECTION

(71) Applicant: Mazor Robotics Ltd., Caesarea (IL)

(72) Inventor: Ido Zucker, Tel Aviv (IL)

(73) Assignee: Mazor Robotics Ltd., Caesarea (IL)

( * ) Notice: Subject to any disclaimer, the term of this patent is extended or adjusted under 35 U.S.C. 154(b) by 657 days.

(21) Appl. No.: 17/499,765

(22) Filed: Oct. 12, 2021

(65) Prior Publication Data

US 2022/0142709 A1 May 12, 2022

Related U.S. Application Data

(60) Provisional application No. 63/113,088, filed on Nov. 12, 2020.

(51) Int. Cl.
*A61B 34/30* (2016.01)
*A61B 34/10* (2016.01)
(Continued)

(52) U.S. Cl.
CPC .............. *A61B 34/10* (2016.02); *A61B 34/30* (2016.02); *G16H 20/40* (2018.01); *G16H 50/70* (2018.01);
(Continued)

(58) Field of Classification Search
CPC .................... A61B 34/10; A61B 34/30; A61B 2017/00261; A61B 2034/107;
(Continued)

(56) References Cited

U.S. PATENT DOCUMENTS

2007/0249911 A1   10/2007  Simon
2014/0081659 A1*   3/2014  Nawana ................. G16H 10/20
                                                                    705/3
(Continued)

FOREIGN PATENT DOCUMENTS

WO   WO 2020/180566   9/2020

OTHER PUBLICATIONS

Invitation to Pay Additional Fees for International (PCT) Patent Application No. PCT/IL2021/051293, dated Feb. 23, 2022, 13 pages.

(Continued)

*Primary Examiner* — Sohana Tanju Khayer
*Assistant Examiner* — Dylan M Katz
(74) *Attorney, Agent, or Firm* — Sheridan Ross P.C.

(57) ABSTRACT

Systems and methods for automated path planning of a surgical procedure, such that the optimal approach is selected from among a series of potential choices. The system is configured to plan and carry out, using a robotic surgical system, access to a surgical site starting from selection of the skin entry point. The methods select the best surgical approach and plan the physical path for robotically performing a selected surgical procedure. The path finding method uses preoperative MRI or CT images and computer vision or other image processing method to identify specific organs and tissues. The method then assigns values to a variety of parameters that define the tissue compressibility, penetrability, flexibility, and other characteristics. The system then plans an optimal path to reach the surgical target area with minimum danger of tissue damage and maximum patient safety, and encodes this information for execution by a robotic system.

20 Claims, 7 Drawing Sheets

(51) Int. Cl.
  G16H 20/40  (2018.01)
  G16H 50/70  (2018.01)
  G16H 70/20  (2018.01)
  *A61B 17/00*  (2006.01)

(52) U.S. Cl.
  CPC .... G16H 70/20 (2018.01); *A61B 2017/00261* (2013.01); *A61B 2034/107* (2016.02)

(58) Field of Classification Search
  CPC ........ A61B 2090/065; A61B 2090/374; A61B 2090/376; A61B 2090/3762; A61B 2090/378; A61B 34/32; G16H 20/40; G16H 50/70; G16H 70/20; G16H 30/40; G16H 50/20; G06N 20/00
  See application file for complete search history.

(56) References Cited

U.S. PATENT DOCUMENTS

| | | | | |
|---|---|---|---|---|
| 2016/0070436 A1* | 3/2016 | Thomas | ................ | G06T 7/0012 715/771 |
| 2019/0262084 A1* | 8/2019 | Roh | ....................... | G16H 20/40 |
| 2020/0275976 A1 | 9/2020 | McKinnon et al. | | |
| 2020/0315708 A1 | 10/2020 | Mosnier et al. | | |
| 2021/0394453 A1* | 12/2021 | Lalonde | ................. | B33Y 30/00 |
| 2022/0000556 A1* | 1/2022 | Casey | .................... | G16H 50/50 |

OTHER PUBLICATIONS

International Search Report and Written Opinion for International (PCT) Patent Application No. PCT/IL2021/051293, dated Apr. 19, 2022, 23 pages.

U.S. Appl. No. 17/476,166, filed Sep. 15, 2021.

Mobbs et al. "Lumbar interbody fusion: techniques, indications and comparison of interbody fusion options including PLIF, TLIF, MI-FLIF, OLIF/ATP, LLIF and ALIF," Journal of Spine Surgery, 2015, vol. 1, No. 1, pp. 2-18.

Baek et al. "Path Planning for Automation of Surgery Robot based on Probabilistic Roadmap and Reinforcement Learning," IEEE, 2018 15th International Conference on Ubiquitous Robots (UR), Jun. 26-30, 2018, 7 pages.

* cited by examiner (REFERENCE; Mobbs et al. Fig 1)

SURGICAL PATH PLANNING USING ARTIFICIAL INTELLIGENCE FOR FEATURE DETECTION

CROSS REFERENCE TO RELATED APPLICATIONS

This application claims priority to U.S. Provisional Application No. 63/113,088, filed on Nov. 12, 2020, and entitled "Surgical Path Planning Using Artificial Intelligence for Feature Detection", the entirety of which is hereby incorporated by reference.

FIELD

Embodiments of the present disclosure are generally related to the field of robotic surgery, especially for use in planning the optimal path for reaching the target tissue in spinal operations.

BACKGROUND

Degenerative disease of the spine is a major cause of disability in the aging population. Vertebral pathology such as degenerative disc disease or abnormal motion of spinal segments relative to each other often results in debilitating pain. Fusion of adjacent vertebrae with insertion of man-made interbodies to replace a degenerated disc can relieve a significant amount of the preoperative pain. The success of spinal fusion operations may range from 60-70% and is dependent on a number of factors, including the skill of the surgeon. Other contributing factors to the success of a spinal fusion are individual characteristics of the patient, the number and location of vertebrae to be fused, the type of hardware selected, and the surgical approach. The five primary lumbar interbody fusion (LIF) approaches are: anterior (ALIF), lateral or extreme lateral interbody fusion (LLIF or XLIF), oblique lumbar interbody fusion/anterior to psoas (OLIF/ATP), transforaminal (TLIF or MI-TLIF), and posterior (PLIF). Each of these approaches has advantages and disadvantages, and varying rates of success. In the context of this application, the term 'approach' refers to a specific surgical method or technique, in contrast to a physical path, or a movement closer to a target. This distinction is important, in order to distinguish this use of the term "approach", from the alternative meaning of a particular path chosen from the entry point on the skin to reach the surgical target, which is also discussed in the application.

The specific approach selected for a spinal fusion may depend on both the clinical status and physical characteristics of the patient, as well as surgeon preference. The fact that there are so many possible approaches suggests that no single approach is ideal for each application. A given approach may be preferable for a thin patient as compared to one who is grossly overweight, or for a specific vertebral level, or for a patient with pre-existing conditions such as asthma or other respiratory insufficiency. The learning curve for spinal fusion is difficult and requires months or years of practice to become proficient in a given technique or approach. Thus, the multiplicity of options may lead to suboptimal outcomes, as it is not possible for a single surgeon to master all approaches with equal efficiency. It is thus probable that some patients have less than optimal outcomes because of the limits of human expertise. Typically, a surgeon selects the approach that he/she has most experience in performing and feels the most comfortable with, rather than basing the choice of approach on the most likely to succeed, out of the several options possible for a given patient.

Documents pertaining to planning the surgical approach to spinal fusion, or for planning the path or positioning of an instrument to be inserted into a patient, include:

"Lumbar interbody fusion: techniques, indications and comparison of interbody fusion options including PLIF, TLIF, MI-TLIF, OLIF/ATP, LLIF and ALIF." R J Mobbs, K Phan, G Malham, K Seex, and P J Rao. J Spine Surg. 2015 December; 1(1): 2-18. doi: 10.3978/j.issn.2414-469X.2015.10.05.

"Path Planning for Automation of Surgery Robot based on Probabilistic Roadmap and Reinforcement Learning," D Baek, M Hwang, H Kim and D S Kwon, presented at the 15th International Conference on Ubiquitous Robots, June 2018.

SUMMARY

Embodiments of the present disclosure generally relate to methods of planning robotically-controlled insertion of a surgical instrument or hardware to be implanted. Though the methodology is applicable to any region of surgical intervention, these embodiments use the example of spinal surgery to illustrate the methods and techniques proposed, spinal surgery being a particularly complicated field because of the problems of access to the surgical site, and the sensitivity of the organs close to the operating site, such as the spinal cord, spinal nerves, and the major blood vessels in the vicinity.

A large amount of clinical data has been acquired over the past several decades regarding the success of various approaches to interbody fusion. Individual surgeons generally select the method with which they are most familiar. Some approaches may be more suitable for a given type of patient, based on a variety of factors such as vertebral levels to be fused, body type, age, and other clinical factors. For various approaches, the patient needs to be positioned on the operating table in a supine orientation; for other approaches, the patient is positioned in a lateral or prone position. Once a particular approach has been selected and the operation is in progress, it is difficult if not impossible to change the type of procedure. Thus, the selection of the optimal approach pre-operatively is important. It would thus be beneficial to automate the methodology for selecting the best technique for spinal fusion, such that the specific approach chosen and the unique path from origin to target region, would be selected to achieve the best possible outcome for a given patient, regardless of the individual experience and skills of the surgeon. To make this determination, algorithms of artificial intelligence (AI) may be applied to a number of data sources, comprising for example, clinical outcomes from previous operations, clinical data from the patient, and other derived and calculated outcomes. These clinical data may be compiled from insurance databases, health organizations, or other sources. The processed data from the AI analysis may be stored in available storage such as in the cloud, through a cloud application programming interface, for access by the system when analyzing data from a new patient, in order to make a determination of the best surgical approach and plan for the procedure.

The system is capable of looking at the tissues that the tool passes through on its way from the entry point on the skin to the target point on or between the vertebrae, and to recognize which tissues are permissible to move and with how much pressure, which ones should not be moved or even touched, which are safe to cut or even remove, and how much is removable. These determinations are made using AI algorithms, as further detailed in the Detailed Description hereinbelow. In one exemplary implementation, the system is used for planning an operation for interbody insertion. As is mentioned in the Background Section, several anatomical approaches exist for insertion of an artificial disc or interbody. These methods include gaining access to the vertebral column from anterior, lateral, or posterior anatomical approaches. Some of these approaches require removal of the vertebral lamina, or the vertebral facet, in order to find a path to insert the interbody. The system therefore needs to plan how much of the bone is necessary and safe to remove in order to be able to insert the interbody. Also, if during the course of the operation, the location of the vertebral bodies shift relative to one another, or relative to the tracking system, the system must take this shift into account, to determine whether and how to change the position of the tool and the interbody to be inserted. The optimal path is not necessarily linear. In the field of robotics, finding the optimal path for interbody insertion involves use of an algorithm for planning motion through a milieu of obstructions or impediments which would negate the use of a simple direct insertion motion. Such algorithms are known as the navigation problem or the piano mover's problem, for finding a sequence of valid steps that moves the robotic end effector from the source outside the body to its destination in the intervertebral disc space, through the environment with the obstructions. In this case, the problem to be solved is for inserting the interbody, held and maneuvered by the end effector or the surgical tool.

In planning the surgical procedure, the plan must take into account the amount of spinal lamina or pedicle to be removed in order to allow insertion of the interbody between the vertebral bodies. As removing bone weakens the spinal column, the quantity and location of removable bone must be determined with consideration of multiple factors in addition to simplifying the ease of interbody insertion.

Two main factors require consideration during the planning stage of planning the tool or instrument path. The first factor is the spinal column and how much bone must be removed, if at all, at the site of interbody insertion. The second factor is the approach to be taken. Each of the five generally known lumbar interbody fusion approaches has advantages and disadvantages, depending on a number of factors such as vertebral levels to be fused, concurrent medical conditions of the patient, prior abdominal surgery with adhesions, anatomical aberrations, or spondylolisthesis. The known approaches to spinal surgery requiring access to the intervertebral disc space, can be divided into two major categories: anterior, which access the spinal column through the soft tissues of the abdomen and reach directly to the intervertebral space; and posterior, which require dissection of the posterior paraspinal muscles and removal of vertebral lamina and/or spinal processes to access the intervertebral disc space. Implementations of the methods and systems disclosed in this disclosure relate to planning access from the anterior direction, while planning access from the posterior direction is disclosed in co-pending U.S. Prov. App. No. 63/106,047 "3-Dimensional Planning of Interbody Insertion", having a common inventor with the present application, and incorporated by reference.

In an anterior approach, the surgeon should perform a segmentation analysis to know which tissues can be moved, and which not, which can be removed or incised, and which not. For each tissue, the system should learn the allowed procedures that can be performed on each tissue and how to carry out that procedure. The system learns about each tissue by both preoperative programming and by intraoperative exploration. For the preoperative stage, each tissue is identified and labeled with known parameters, such as density, friability, vascularity, essentiality for life, movability and other factors. The system calculates a score that determines if and how much the tissue can be moved, cut, poked, retracted, or the like, as further discussed in the above mentioned co-pending U.S. Prov. App. No. 63/106,047 "3-Dimensional Planning of Interbody Insertion", assigned to the present applicant.

The details of one or more aspects of the disclosure are set forth in the accompanying drawings and the description below. It is to be understood that the scope of the methods revealed in this disclosure are applicable to many types of surgical path planning, comprising at least operations of the abdominal and thoracic cavities, as well as procedures requiring deep tissue dissection and careful avoidance of critical structures not visible by direct and open observation or by endoscopic photography, such as of the neck, throat, and skull base. One exemplary implementation is thus described in detail, specifically in regard to planning the optimal surgical approach for spinal interbody fusion, with other possibilities suggested in brief. Additional features, objects, and advantages of the techniques will be apparent from the description and drawings, and from the claims.

There is thus provided in accordance with an exemplary implementation of the devices described in this disclosure, a method for automatically planning a tool path through tissues to a surgical target in the spine of a subject, the method comprising: (a) performing image segmentation on a set of three-dimensional medical images of a region of possible paths to the surgical target, to define boundaries of tissues located in the region of the possible paths; (b) selecting an entry point for a first planned path from the entry point to the surgical target; (c) using information relating to a combination of known tissue parameters to assign to each tissue in the first path, a weighting value for tissue traversability; (d) using the weighting values for tissue traversability, calculate a cost function of the first path, taking into account: (i) the sum of weighted values for tissue traversability of all tissues along the planned first path; and (ii) the clinical status of the subject; (e) repeating steps (b) to (d) for additional entry points and associated paths; and (f) selecting the path with the minimum cost function. The method may further comprise the steps of: (g) providing the planned tool path to a robotic controller, and (h) using the robotic controller to move the tool through the tissue according to the planned tool path to reach the spinal surgical target.

There is also provided in accordance with an exemplary implementation of the devices described in this disclosure, a system for planning a safe path for robotic execution of a surgical procedure on the spine of a subject, comprising: at least one processor executing instructions stored on at least one non-transitory storage medium to cause the at least one processor to: a) access a database containing analyses of outcomes of surgical procedures on the spine of patients in a reference population; b) using the outcomes accessed in the database of patients having a similar clinical profile to that of the subject, select the surgical procedure most likely to produce a desired outcome for the subject; c) select from a set of known surgical approaches, the surgical approach expected to be optimal for executing the selected surgical procedure; and d) using a segmented three-dimensional image set annotated with predetermined tissue traversability of tissues in the region of the selected surgical approach, plan paths for robotic access of at least one surgical tool to the spine, for execution of the selected surgical procedure, wherein the optimal planned path is one which minimizes interaction of the at least one surgical tool with tissues having unfavorable traversability data.

There is also provided in accordance with an exemplary implementation of the devices described in this disclosure, a system for robotic execution of a planned procedure path using a preselected surgical approach on a subject, comprising: a) at least one processor executing instructions stored on at least one non-transitory storage medium to cause the at least one processor to implement robotic execution of the planned procedure path on the subject; b) a memory comprising the planned procedure path, and tissue traversability data that indicate a risk of interacting with each specific tissue along the planned path; and c) at least one sensor configured to provide input to the processor to update the tissue traversability data intraoperatively; wherein the input is used to update the planned procedure path intraoperatively to avoid tissues with unfavorable traversability data.

There is further provided in accordance with an exemplary implementation of the devices described in this disclosure, a system for selecting a specific surgical procedure to be performed on a subject having a clinical condition for which intervertebral disc removal is indicated, comprising: at least one non-transitory storage medium for storing instructions; and at least one processor executing the instructions stored on the at least one non-transitory storage medium, the processor performing: i) classify clinical parameters and surgical outcome data from patients in a reference population, each patient having undergone a surgical procedure for intervertebral disc removal using any one of a set of known surgical approaches; ii) match clinical parameters of the subject to a subgroup of the reference population having an equivalent clinical condition to that of the subject; and iii) based on the classified outcome data of patients in the matched subgroup, select the specific surgical procedure and surgical approach predicted to result in an optimal outcome for the subject.

There is further provided in accordance with an exemplary implementation of the devices described in this disclosure, a method for selecting a surgical approach for either disc replacement or spinal fusion on a subject, the method comprising: i) classifying clinical parameters and surgical outcome data from patients in a reference population, each patient having undergone either disc replacement or spinal fusion using one of a number of surgical approaches from either an anterior category or a posterior category; ii) matching clinical parameters of the subject to a subgroup of the reference population having a similar clinical condition to that of the subject; iii) using an influence of the clinical parameters of the subject on the desirability of either the anterior category or the posterior category in order to determine which category is preferred for the subject; and iv) based on the classified outcome data of patients in the matched subgroup, and taking into account the preferred category, selecting one of the number of surgical approaches; wherein the selection takes into account both the surgical outcome data and the preferred category in order to select the surgical approach most likely to result in a favorable outcome of the disc replacement or the spinal fusion.

Definitions

Image segmentation: Image segmentation is the process of partitioning a digital image into multiple segments (sets of pixels, also known as image objects). The goal of segmentation is to simplify and/or change the representation of a complex image into something that is more meaningful and/or easier to analyze.

Spinal segmentation: Spinal segmentation is a subset of image segmentation providing information specifically about the vertebral column, beyond that routinely obtained in image segmentation. In the process, three-dimensional images of a patient's spine are analyzed using image segmentation and various spinal parameters measured. The segmentation output is then used to develop specimen-specific finite element models, and may be used in conjunction with kinematic data acquired during biomechanical testing to investigate intervertebral joint behavior. Spinal segmentation thus provides for obtaining additional information with regard to the behavior of specific joint features under various loading conditions, and this information is then available for use in pre-operative planning of a surgical procedure.

Lumbar interbody fusion: A surgical operation to fuse two or more lumbar vertebrae in a procedure requiring the insertion of an artificial disc or interbody, with or without a biological bone graft, between the bodies of two vertebrae being fused. Five main surgical approaches have been developed for carrying out these procedures.

Computer vision: is a field of artificial intelligence that uses digital images from cameras and videos and deep learning models to train computers to accurately identify and classify objects. In this application, the digital images are primarily static medical images such as MRI and CT, and live, intraoperative three dimensional videography from ultrasound or optical imaging.

DETAILED DESCRIPTION

Figures 1A, 1B:
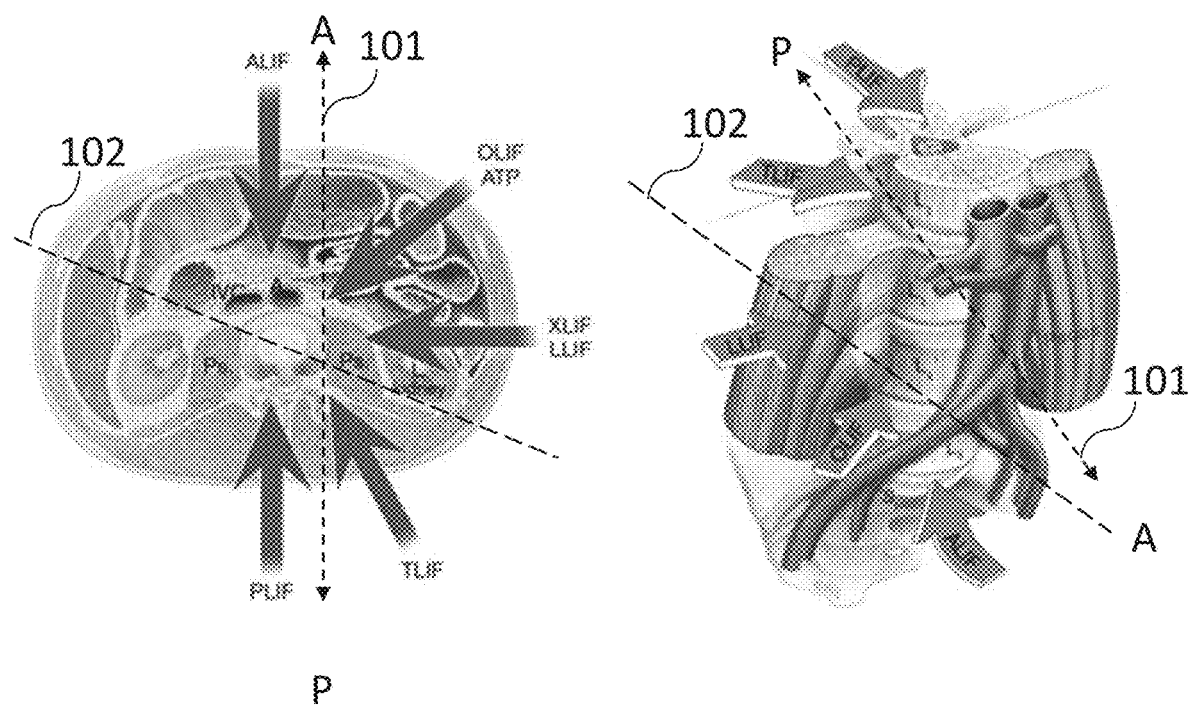
FIGS. 1A-1B illustrates schematically the five major surgical approaches to intervertebral fusion.

Reference is now made to FIGS. 1A and 1B, showing diagrams illustrating five current approaches to lumbar interbody fusion. FIG. 1A shows a cross-sectional view of the abdomen and spine, and FIG. 1B shows an isometric view of the spinal column and adjacent muscles. The diagrams are published in the article by Mobbs et al. cited in the Background. Anterior and posterior directions are marked by A and P respectively, and the A-P axis in each diagram is indicated by a dotted, double-headed arrows 101. The five lumbar interbody fusion approaches illustrated in these figures are anterior (ALIF), oblique/anterior to psoas (OLIF/ATP), lateral/extreme lateral (LLIF/XLIF), posterior (PLIF), and transforaminal (TLIF), of which ALIF, OLIF, and LLIF are performed with the patient in a supine or lateral position; and PLIF and TLIF are performed with the patient positioned in a prone position. These positional differences mean that surgical approaches that traverse the patient anterior to the spinal column, indicated by the dashed lines 102, will need to deflect soft tissue organs in abdominal and pelvic cavity, whereas posterior surgical approaches have a need to traverse muscle and bone. The plethora of approaches attests to the difficulty of access to the spinal column, because of the internal positioning of this critical organ. Added to the anatomical challenges is the reality of human error, even among the most qualified surgeons, and the length of training time required to learn a specific approach well, such that no surgeon can be an expert at all five approaches. For at least these reasons, it could greatly improve surgical outcomes if a standard and automated method of selecting the best approach and of planning the optimal path to the target were to be developed. Such a method would optimally be a) based on specific characteristics of each individual patient, b) sufficiently automated that it would not be strongly dependent on surgeon training or lack thereof, and c) applicable to any known lumbar interbody fusion approach.

Figure 2:
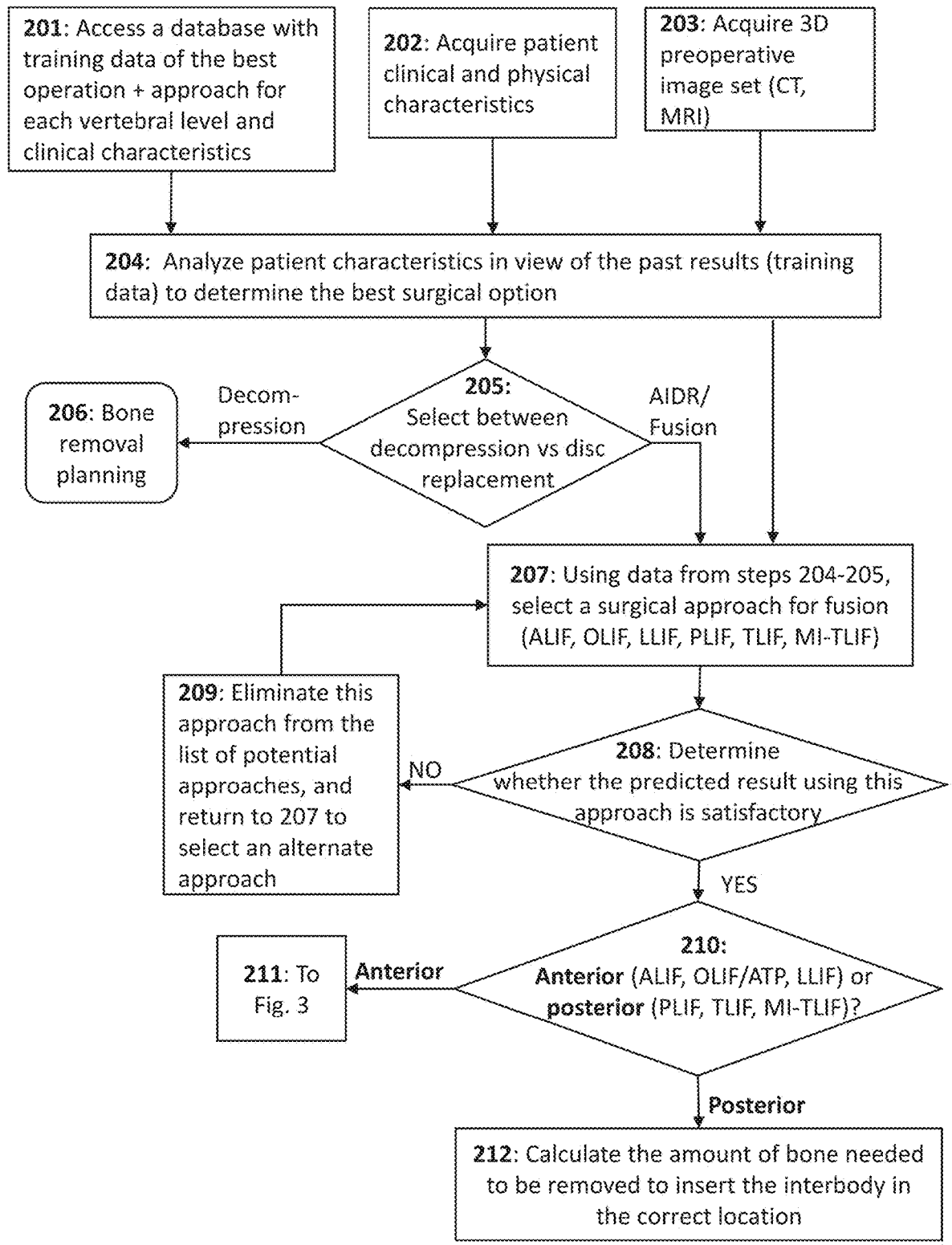
FIG. 2 is a flow diagram that illustrates the steps involved in an exemplary implementation of the method.

Reference is now made to FIG. 2, illustrating an exemplary flow of information in an initial planning phase of patient evaluation for a reparative spinal column procedure using one of the surgical approaches discussed herewithin above. In step 201, training data is produced and made available to the system. These training data are produced by artificial intelligence analysis of a database comprising past clinical outcomes on a reference population of prior patients who had interbody lumbar fusion or artificial intervertebral disc replacement (AIDR), using various surgical approaches. Clinical outcomes on the reference population may be obtained from hospital records, health maintenance organization or insurance company records, or other sources of anonymous medical data. The outcomes are sorted based on patient clinical data, vertebral level to be fused, and other clinical data, such that future patient data can be input to the artificial intelligence algorithms and each patient sorted according to the procedure most likely to produce a successful long-term outcome. In these analyses, patients with similar conditions are taken as a group, wherein 'similar' may define, e.g., subjects having a bulging or herniated disc at any lumbar level on either right or left side. Concentric subgroups of lesser or greater similarity may be useful for some analyses of clinical outcomes, e.g., a herniated disc at a specific vertebral level. A greater degree of similarity would tend to enhance the specificity and usefulness of the analysis, as long as sufficient numbers of patients were available to make the analysis statistically relevant.

In step 202, patient data is collected, which could typically comprise the level of vertebral pathology and proposed diagnoses thereof, with possible surgical solutions thereto, in combination with at least some of the patient's weight, height, body mass index, smoking status, level of vertebral pathology, diagnosis, bone density as determined by Z-score, serum levels of vitamin D and creatinine, pulmonary function tests, stress test result, and EKG.

In step 203, at least one preoperative three-dimensional image set, using imaging modalities such as CT, MRI or both, is acquired.

In step 204, the patient characteristics, clinical values, image sets, and other data determined in step 202, are analyzed in the light of the possible surgical options determined from the database used in step 201, to determine the source of the pain, and thus the best treatment option, as further described in the co-pending U.S. Prov. App. No. 63/106,047 "3-D Planning of Interbody Insertion", assigned to the present applicant.

In step 205, if the surgical procedure indicates that a decompression rather than either a spinal fusion or AIDR should be undertaken, the surgeon may decide to use a different method of path planning, other than the implementation now followed in the flowchart of FIG. 2. In such a case, the method terminates in step 206, moving to methods detailed for disparate options for surgical intervention and path planning as further detailed in the co-pending U.S. Prov. App. No. 63/106,047 "3-D Planning of Interbody Insertion" assigned to the present applicant. In other implementations, the method may begin only once the choice of a spinal fusion operation has already been selected. Continuing from step 205, in the case that a spinal fusion is decided upon as the surgical method of choice, all of the elements that comprise this decision from steps 201 to 205 are input at step 207, and integrated to generate the decision as to which surgical approach is to be used for the fusion.

In step 207, the favored surgical approach is selected for the given patient's needs using processed data from steps 204 and 205. The surgical approach may be used for spinal fusion, AIDR, or other procedure that requires access to the intervertebral disc. The output from step 205, comprising a weighted list of the relevant medical risk factors, such as co-existing conditions that increase risk of anesthesia, other bone diseases, prior operations), and categorization of the patient in terms of likelihood of long term success for a given procedure, is used to select a preferred surgical approach for lumbar interbody fusion, among the five known surgical approaches PLIF, TLIF, MI-TLIF, OLIF/ATP, LLIF, or ALIF. For example, depending on the level of the spinal pathology, and due to the presence of major blood vessels in the lumbar area, the ALIF approach is suitable for levels L4/L5 and L5/S1. On the other hand, the ALIF approach is limited for L2/3 and L3/4 because of the need for extensive peritoneal and kidney retraction and the risk of superior mesenteric artery thrombosis. An ALIF procedure may be recommended for patients with degenerative disc disease or discogenic disease, in the case that an AIDR is the preferred procedure. The ALIF approach allows direct midline view of the disc space and lateral exposure of the vertebral bodies, as well as maximization of implant size and surface area, thus facilitating correction of lordosis and restoration of foraminal height. ALIF also allows sparing of posterior spinal muscles. This approach may be selected for patients who have had a previous posterior spinal fusion requiring revision, to avoid the complications inherent in traversing scar tissue, which may alter the normal relationships among tissues and requires more time and care to dissect. ALIF may also provide for quicker recovery. Contraindications for performing ALIF include prior abdominal surgery with adhesions or vascular anomalies, severe peripheral vascular disease, and high-grade degenerative spondylolisthesis. All of these factors, both indications and contraindications, are stored in the database accessed in step 201. Similar information for each of the other surgical approaches is likewise stored in the database, and used for compiling training data, for use when other approaches are implemented.

In some implementations of the disclosed methods, additional steps are taken to define the optimal surgical approach for lumbar interbody, these steps including: a) obtaining image sets of a region of interest of the spine i) upright in three-dimensions, and ii) in two-dimensions in positions of bending, b) performing spinal segmentation on at least the three-dimensional image set to identify vertebral body boundaries, c) performing kinematic or biomechanical modeling on at least the two-dimensional image set to determine which vertebrae to instrument, and d) providing a database of clinical outcomes of lumbar spinal fusions using each of a selected set of lumbar interbody fusion approaches. In this implementation, clinical data of the patient and outputs of steps a) to d) are used to select, from among the selected set of fusion approaches, the approach most likely to provide an optimal outcome defined by balancing at least two of minimal tissue damage, shortest operative time to reach the surgical target, lowest risk to the patient, predicted short term outcome, and predicted long term outcome.

In step 207, if one of the anterior surgical approaches is selected, i.e., ALIF, OLIF, or LLIF, the method proceeds to step 209, further discussed in FIG. 3 herewithin below. Each approach has a general path of access to the target region, starting from either an anterior, lateral, oblique or posterior entry point on the skin, through which the surgical tools and implant must pass to reach the target region. If a posterior surgical approach is selected, i.e., PLIF, TLIF, or MI-TLIF, the method proceeds to step 210.

In step 208, the system determines if the predicted outcome using this approach is satisfactory. A satisfactory predicted outcome may be predetermined by selecting a range of acceptable scores in each category of outputs from step 204. If not performed fully robotically, these decisions are made by the surgeon, using the most preferred outcome of the approach analysis. If the approach is satisfactory, the method proceeds to step 210. If the approach is not satisfactory, the method proceeds to step 209, in which the approach having an unsatisfactory outcome is eliminated from the list of potential approaches, and the method returns to step 207 to select an alternative approach. In some cases, none of the possible surgical approaches may be suitable for a given patient. In such a case, the surgeon or the system may decide to select one of the available options, or may decide to select another treatment option, weighing the risks and benefits to the patient of each option.

In step 210, if the selected approach is TLIF or PLIF, the method proceeds to step 212 calculates how much of each vertebral lamina or processes is necessary and safe to remove in order to insert the artificial interbody. If the selected approach is ALIF, OLIF, or LLIF, the method proceeds to step 211, which segues into the method outlined in FIG. 3.

In step 212, details of the method for interbody selection, bone removal planning, and pathfinding through the paraspinal muscles and posterior vertebral elements are determined, comprising a calculation of the amount of bone needed to be removed to insert the interbody to the correct location. In this step, the method also determines what size of interbody is needed based on the vertebral level, patient height and weight, and perhaps other factors. Further details of the posterior surgical approaches and bone removal are described in the co-pending U.S. Prov. App. No. 63/106,047 "3D Planning of Interbody Insertion and Surgical Approach," assigned to the present applicant.

Figure 3:
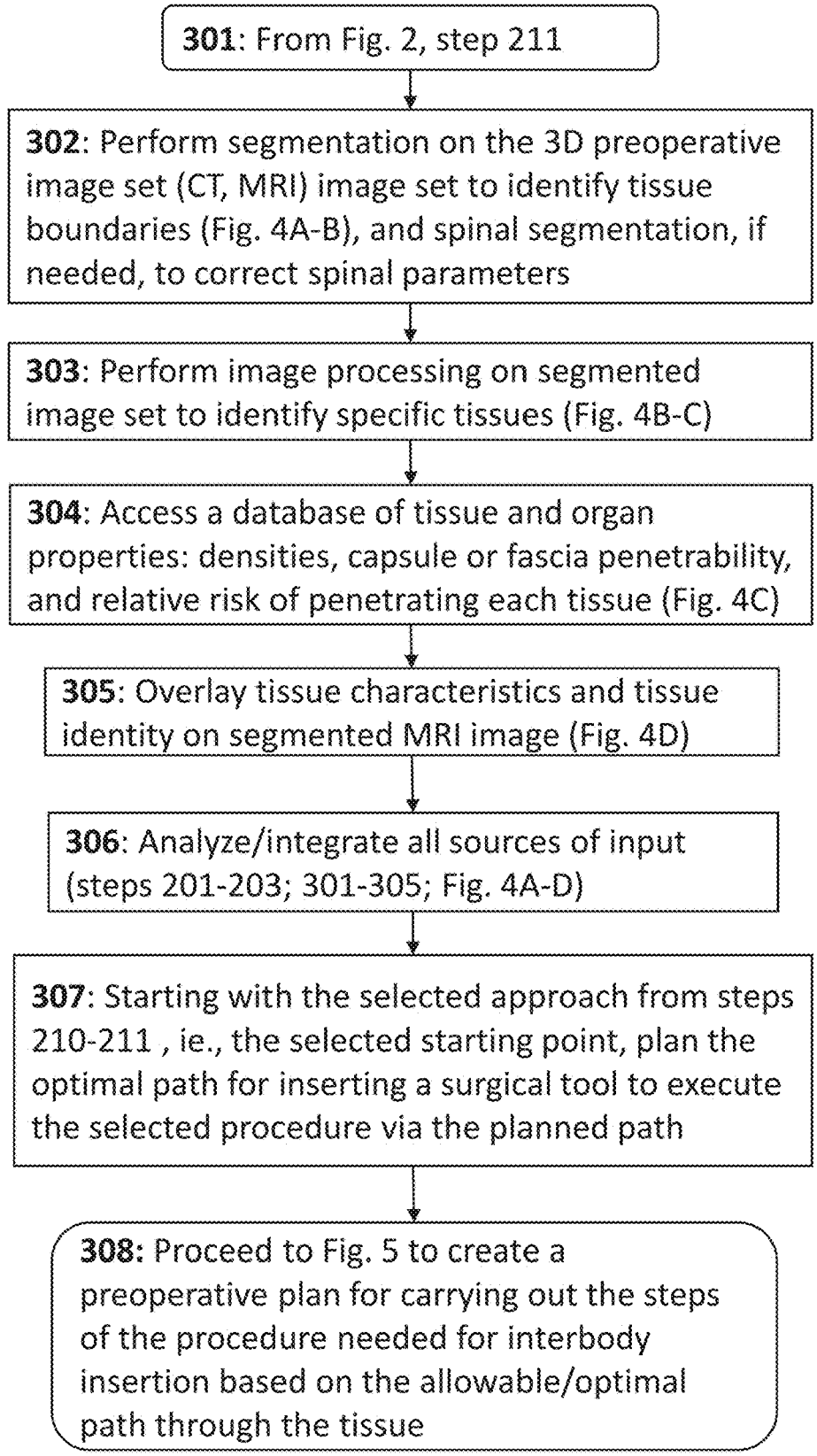
FIG. 3 is a flow chart describing the steps performed in generating a three-dimensional path plan for an individual patient.

Reference is now made to FIG. 3, showing a flow chart of an exemplary implementation of the methods of path planning for an anterior surgical approach to the vertebral column described in the present disclosure, carrying on in step 301 from FIG. 2, step 211 above. While the input so far discussed for the approach decision has been based on the patient's overall clinical situation, background illnesses and database analysis to suggest possible approaches, additional input must now be used, in which the specific clinical status and positions of the tissues and organs of the patient, must be considered in order to successfully accomplish the optimal surgical approach.

A second set of inputs for the exemplary method shown in FIG. 3 is therefore used, starting with step 302, in which an image segmentation procedure is performed on the image set to identify tissue boundaries in the three-dimensional preoperative image set of the surgical region of interest acquired in FIG. 2, step 203.

In step 303, image processing is performed on the segmented images to identify and label specific tissues. In some implementations of the method for spinal fusion requiring alignment of scoliotic or slipped vertebrae, a further in-depth spinal segmentation analysis is carried out at this point, which may include biomechanical modeling or kinematic analysis of the spine in positions of bending, for example, to determine surgical manipulations required to align a spine with abnormal curvatures, as part of planning the surgical approach.

In step 304, the system accesses a database of tissue and organ properties comprising at least some of tissue densities, friability, capsule or fascia strength, innervation, and relative risk of penetrating each tissue. Known values from the literature of various tissues in humans and other species are stored in the database, and this information is applied to the patient's processed images using computer vision and other AI algorithms. Experimental data from human cadaveric tissue or that of other species may also be used as input to the database. The information from this database of tissue and organ characteristics is used to annotate the segmented tissue outlines from step 303.

In step 305, the tissue parameters from step 304 are attributed to the tissues identified in the segmented MRI or CT images, such that each organ or tissue is labeled with its individual characteristics, as further described in FIGS. 4A to 4D below.

In step 306, the various sources of input from steps 201 to 203, and 301 to 305, are analyzed and integrated. In this implementation, the analysis in step 306 uses machine learning algorithms and other forms of artificial intelligence, training, and programs such as probabilistic roadmaps and reinforcement learning. The output of these methods are applied to mathematical functions, as further described for the path-planning algorithm in FIG. 6.

In step 307, a second phase of the method begins. Using the surgical approach selected in step 207, the system plans the optimal path for opening the tissue, providing access to the surgical target site by inserting a surgical tool to open the space, and ultimately, for inserting tools for clearing the intervertebral space, cleaning the vertebral endplates, and carrying the interbody for insertion between two vertebrae to be fused. This step uses input from step 304 and FIGS. 4C and 4D, comprising tissue densities, capsule or fascia penetrability, and relative risk of penetrating each tissue type, and from the processed images in FIG. 4B and 4C to plan a route to the target site. Output from this step comprises at least some of 1) an estimation of the success of this approach, based on a database of past clinical outcomes, 2) the expected time required from initiation of the procedure to target access, 3) estimation of risks involved, and, if relevant, 4) particular points of caution based on the subject's clinical history. These responses may be quantified and tabulated, such that the results are provided to the surgeon for further consideration.

Finally, in step 308, the method plans a path for tool insertion to access the surgical site, preparing for the final step of designing a preoperative plan for carrying out each step of the procedure needed for interbody insertion, for execution by a surgical robotic system, as further described in FIGS. 5A to 5D. Whereas the steps of the exemplary method illustrated in FIGS. 5A to 5D are pre-planned before the operation, according to another exemplary method, the system is configured to allow modifications of the method during the surgical procedure, using feedback and input from sensors, intraoperative imaging, and the surgeon. The sensors may comprise any or all of an externally situated internal imaging device, a pressure detection sensor, a Doppler flow sensor, an endoscopic camera, a mechanical tonometer, a digital indurometer, a fibrometer, or an ultrasound probe.

Figure 4A:
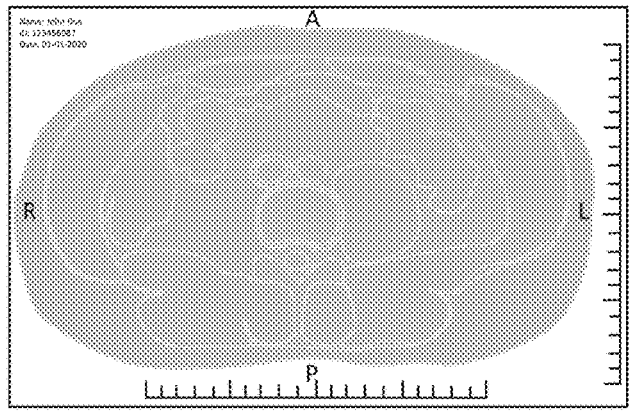
FIGS. 4A-4D are a series of schematic diagrams that illustrate the medical imaging and computational analysis procedures in an exemplary implementation of the method, used to generate a three-dimensional map of the individual patient for path planning.

Reference is now made to FIGS. 4A-D, illustrating an exemplary implementation of the methods of the present disclosure. FIG. 4A represents a transverse MRI image taken through the abdomen at the level of the L3 vertebra. The entire MRI image set comprises many of these transverse sections taken at intervals of 1 cm or less, which may be reassembled to create a three-dimensional image set. Additional images in the coronal and sagittal planes may be incorporated to create a more complete virtual three-dimensional representation of the patient's internal anatomy. While the identity of specific organs is not always obvious based on the T1 and T2 weighted images produced by MRI scanning, a physician skilled in reading these images is able to determine which elements represent individual organs, and to discuss this information with the surgical team for planning the surgical operation. Even so, some elements in an MRI image may be indeterminate.

Figure 4B:
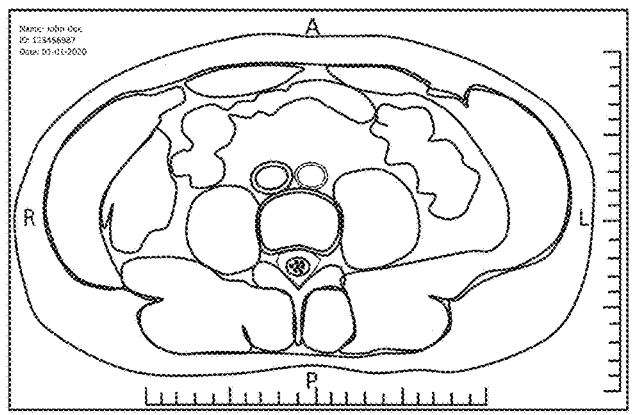

In FIG. 4B, a segmentation process, as defined above in the definition section, uses computer vision or another type of image processing to identify the boundaries of organs and tissue planes, and the images are outlined accordingly. In an exemplary implementation of the currently disclosed methods, the MRI image set acquired in FIG. 4A is used as the input. A pre-processing step is carried out using, for example, an available commercial software, followed by image segmentation to define the boundaries of individual organs and tissues.

Figure 4C:
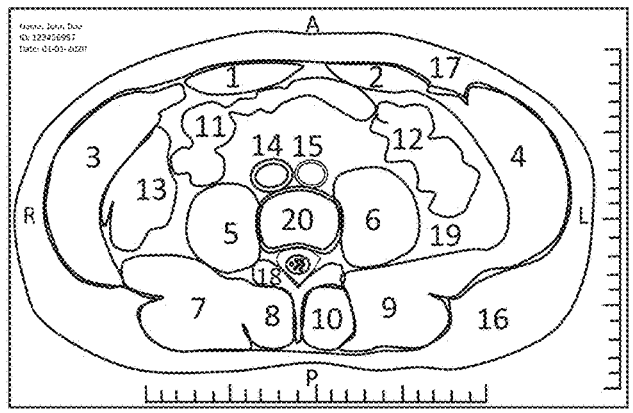

In FIG. 4C, the features outlined by the segmentation process in FIG. 4B are then extracted and classified as individual organs and tissues. In this step, a generally available, annotated database of MRI images may be used to identify the features corresponding to various organs, tissue planes, and other anatomical features of interest. The set of three stacked images on the right side of FIG. 4C represent successive levels of such an exemplary virtual atlas at the anatomical level of the processed patient image shown in the left half of FIG. 4C. In this step, the anatomical features in the processed patient image from FIG. 4B may be labeled with both a number, using the known identifications from the virtual atlas, and with a value corresponding to a particular organ or tissue type. For example, tissues denoted by numbers 1-10 in FIG. 4C, represent specific muscles. Muscles are labeled, and may also be provided with a value representing both general and specific properties and characteristics, such that the system knows which muscles may be moved or retracted, and the amount of tension that may be used on each one, and whether a fascial layer may need to be penetrated in order to move the connected muscle. The vascularity of muscle tissue is a general property, whereas the direction of the muscle fibers in a specific muscle is unique to each muscle or group of muscles.

In FIG. 4C, numbers 11 and 12 identify segments of the small intestine, and 13 is a portion of the colon. Small intestine is generally easily movable, whereas the ascending and descending colon have greater connective tissue attachment and thus cannot be so readily moved. Compared to muscle, the danger of accidentally scoring or incising the surrounding connective tissue or blood supply to these organs, penetrating into the lumen, or exerting undue pressure is a greater risk. Thus, the path planning algorithm takes this information into account when planning the best route through the tissue, by numerically weighting each tissue according to the danger or safety of moving, penetrating, traversing, or removing it. Numbers 14, representing the aorta, and 15, representing the vena cava, are blood vessels that, because of their internal location, are at lower risk of being along a path of surgical access. However, because of their essential nature, and the lethal effect of accidental penetration, the system ensures that the path of access to the target region avoids these structures completely. Numbers 16 and 17 indicate adipose tissue, which because of its ubiquitous and external location in most individuals, will necessarily require penetration during the course of accessing the surgical target site. Number 19 shows the peritoneal cavity, which is a potential space, and into which other organs may be shifted. Number 18 is the vertebral process and 20 indicates the vertebral body of the corresponding vertebra, in this case, L3. The unlabeled tissue between the vertebral body 20 and spinous process 18 is the thecal sac containing the spinal nerve endings. This tissue may be moved within an allowable, predetermined amount, but should never be penetrated. Each tissue, both those illustrated and briefly explained in FIG. 4C, and any others that may be encountered by the surgeon or by a tool of a robotic surgical system during a procedure to provide access to the surgical target, are identified according to the specific tissue type.

Figure 4D:
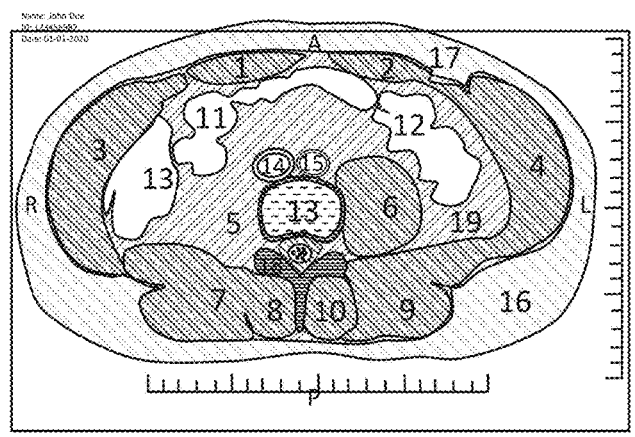

The processed and numerically-weighted image set from FIG. 4C then undergoes further processing as described in FIG. 4D, in which each organ is labeled, as shown here by different shadings, to identify the characteristics of that tissue, comprising at least some of density, vascularity, innervation, compressibility, risk of penetration, friability, movability, elasticity, capsular strength, and other factors. In this step, the same or another database as that used in the step outlined in FIG. 4C is used to assign tissue densities, movability or compressibility of the tissue in question, danger of penetration, extent of safe retraction, and other clinical values. This processing step comprises at least two sources of input. One source is the specific information derived from the individual's MRI image and processed with computer vision or other type of image processing, as described in FIGS. 4B and 4C. A second source of information is a database comprising at least some of clinical and laboratory data on tissue properties of those organs likely to be found in the path of the surgical approach to the target area. Each tissue type, and each specific segment of tissue, is provided with a list of specific characteristics, for example: density, friability, vascularity, essentiality for life, and movability, that enable the system to plan the safest route from the entry point to the surgical site. These parameters are weighted and compiled into a numerical tissue traversability value, or a set of such values.

It is to be understood that many parameters are needed to define an organ or tissue type, not all of which have been listed. Those provided in the present disclosure are exemplary quantifiable characteristics among many that may be used in a given operation. The data may be gathered from various sources, such as from the Database of Tissue Properties to be found at (https://itis.swiss/virtual-population/tissue-properties/overview/). Further information in the tissue property database may comprise, for example, measurements of the compressibility of various tissues. This information may be collected by various devices designed for this purpose: e.g., mechanical tonometer, digital indurometer, or fibrometer. Other types of information in the database are the average (or range of) length of omental tethers or other connective tissue components holding organs in place. The ease with which an organ capsule can be penetrated by a blunt or sharp instrument may also be measured and added to the database, such that the path planning steps take into account the fragility and risk of damage to each organ along the selected approach to the vertebral target area. In some embodiments of the disclosed methods, each parameter may be graded on a numerical scale, such that each tissue is assigned a relative risk of injury compared to other tissues along the selected approach. The scale may be adapted to allow some tissues to be labeled as absolutely forbidden to touch, enter, move, or remove. Another level of tissue evaluation entails specific assessment of a given tissue based on the age and clinical status of the subject. For example, older patients with vascular disease may have tissues that are more friable and susceptible to blunt trauma or retraction. These factors need to be considered and incorporated into the absolute and relative traversability scores for specific tissues of a given subject. In some implementations, the traversability scores are combined to produce a single traversability value for the path, taking into account the weighted values of the various component scores.

Reference is now made to FIGS. 5A to 5D, in which exemplary path planning routes are shown for a lumbar interbody fusion, or for an AIDR procedure. Once the surgical approach has been selected, the method must decide on a detailed path based on this specific approach. The exemplary method shown in these figures uses the processed and reconstructed three-dimensional MRI or CT images from FIG. 4D. Before performing any of the steps shown in these figures, and as further delineated in steps 207 to 211 of FIG. 2, the method collects information and assesses which surgical approach is most likely to be successful for this particular patient. The example shown in FIGS. 5A to 5D illustrates an exemplary path for an anterior approach (ALIF). The axis and orientation of each pair of images are shown, i.e., superior-inferior (S-I), medial-lateral (M-L), right left (R-L), anterior-posterior (A-P). Each organ or tissue is provided with a series of scores indicating its amenability to being traversed, moved, or otherwise manipulated. In each of FIGS. 5A-5D, the illustrated organs are labeled as follows: mediastinum 1, liver 2, large intestine 3, lungs 4, small intestine 5, kidneys 6; major venous 7 and arterial 8 blood vessels of the pelvic area; vertebrae are marked by their unique identity, in which T indicates thoracic and L indicates lumbar.

Figure 5A:
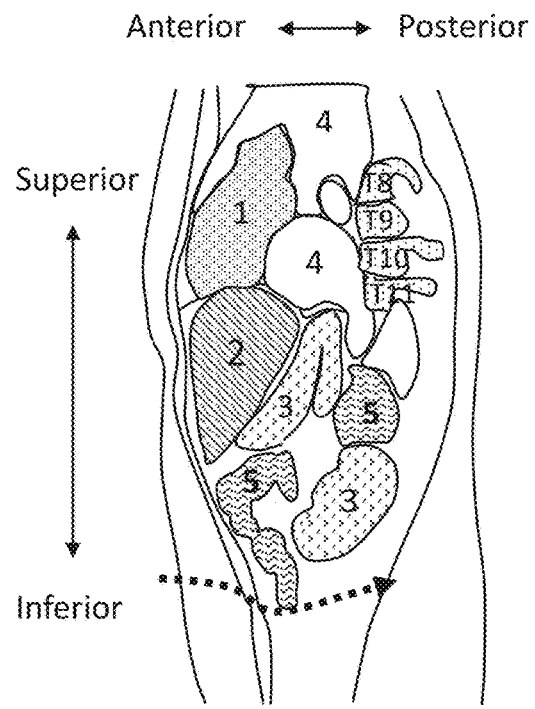
FIGS. 5A-5D provide illustrations of an exemplary implementation of the planned path taken during a robotically controlled interbody fusion procedure.
Figure 5B:
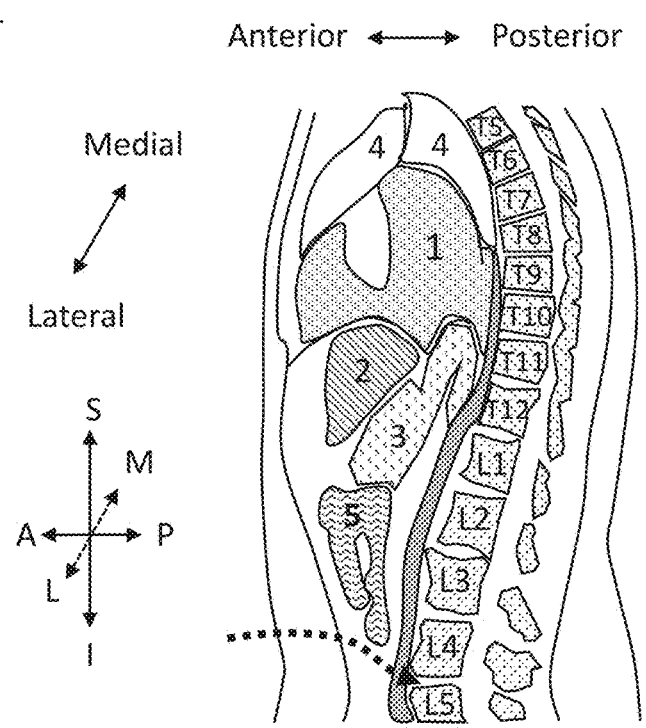
Figure 5C:
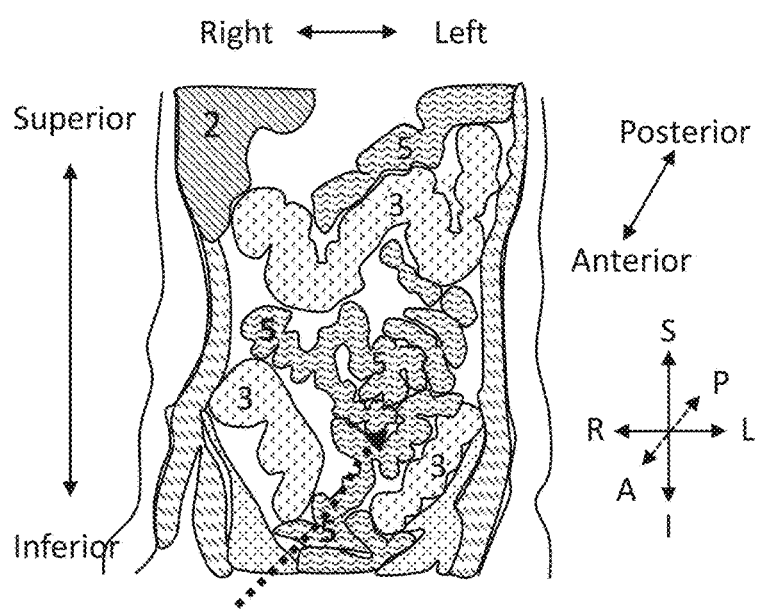
Figure 5D:
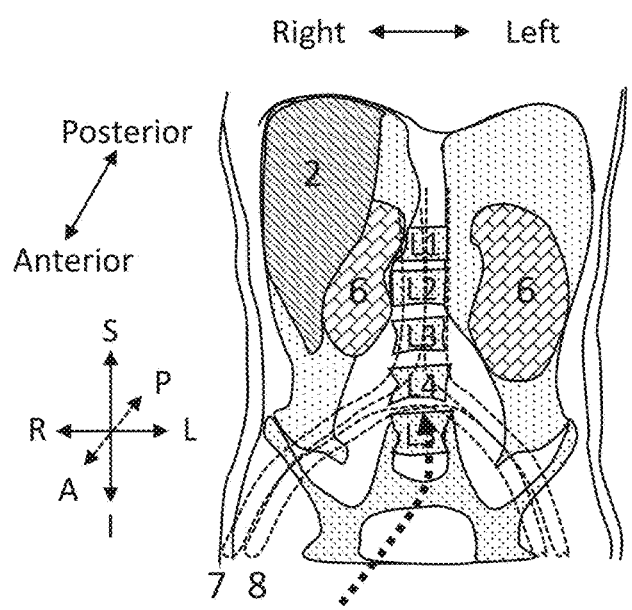

Each of FIGS. 5A to 5D illustrates a two-dimensional representation of the same representative three-dimensional planned surgical path through the torso of the patient, from the entry point to the surgical target. FIGS. 5A and 5B show a lateral view at two depths from the left hand side of the body, such that FIG. 5B is nearer the sagittal midline; FIGS. 5C and 3D show two frontal views at different anterior-posterior depths, such that FIG. 5D is nearer the vertebral column. In actual operation, the system displays the path through the tissue in three dimensions, represented in these figures by the heavy, dotted, curved arrows. The arrows represent a single path viewed from different directions and angles, the calculations for which are further described in FIG. 6 herewithin below. For this exemplary procedure, an L4-L5 interbody fusion using an anterior approach, the patient is prepared and positioned supine. The path illustrated is initiated from the entry point via the lower abdomen. The surgical opening requires cutting the skin and muscles of the abdominal wall (FIGS. 5A, 5B), followed by gentle retraction of the loose, small intestinal loops 5 (FIGS. 5A, 5B, and 5C) to expose the peritoneal wall (not shown), behind which lie the kidneys 6 and vasculature 7, 8 (FIG. 5D). The vasculature requires mobilization and dissection away from the surrounding tissues to enable surgical access to the L4-L5 interbody. In some exemplary implementations, the system may incorporate at least one sensor for detecting pressure applied on the tissue by the surgical end effector, or for testing vascularity of the tissue in the path of the tool, or an optical camera, or an externally situated internal imaging device, or a Doppler or ultrasound sensor for feedback of tissue echolation.

Figure 6:
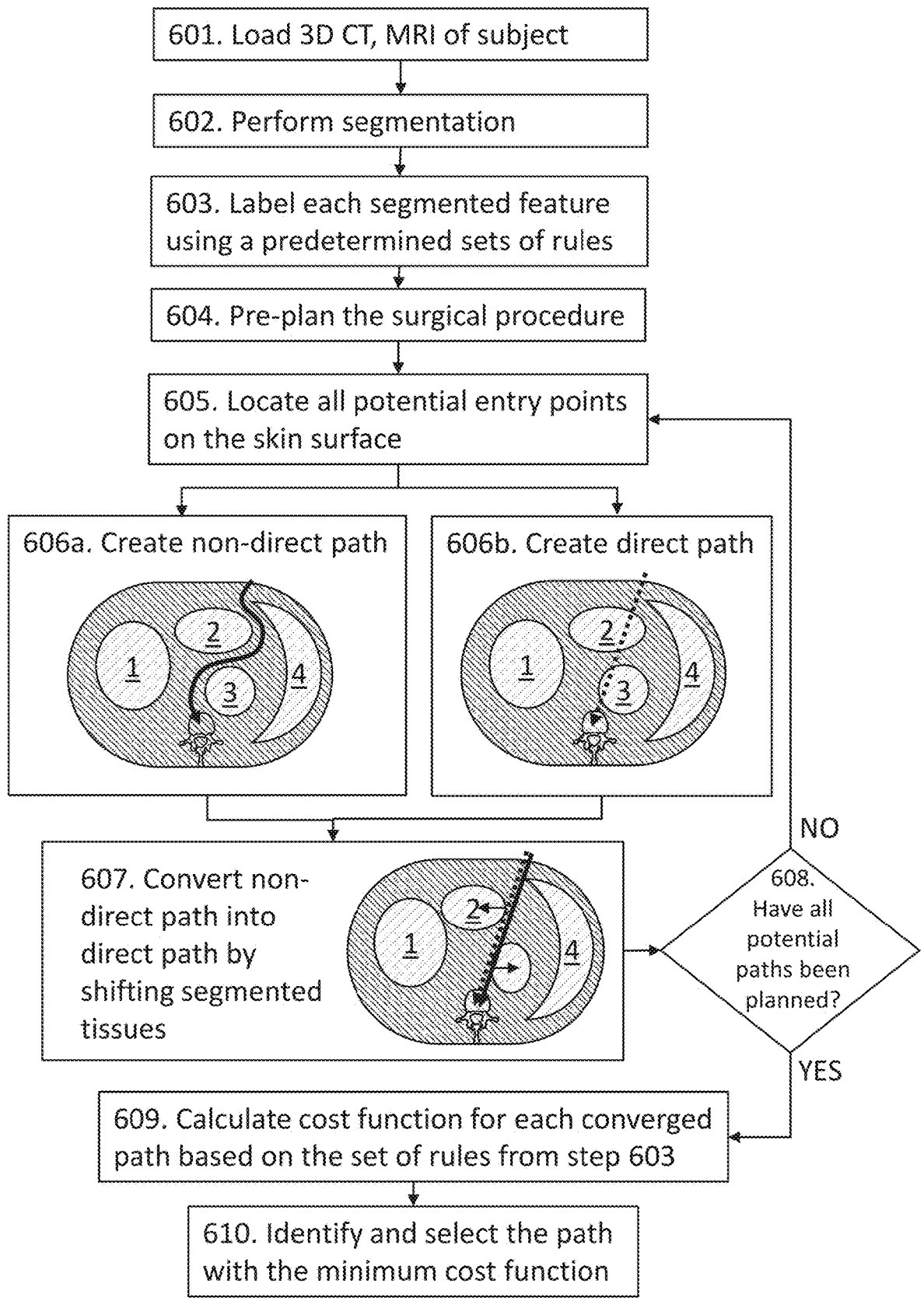
FIG. 6 is a flow chart illustrating an exemplary implementation of an automated pathfinding procedure.

Reference is now made to FIG. 6, which is a flow chart showing details of one exemplary implementation for planning an automated path from entry point to surgical target. In step 601, a three-dimensional image set of at least the operative region of the subject is loaded into the system for analysis. In step 602, the segmentation process of step 302 of FIG. 3, as illustrated in FIG. 4B, is performed, in which bone is distinguished from soft tissue, different bone elements are identified, internal organs are identified and labeled, as well as muscle and adipose tissue.

In step 603, each segmented element from step 602 and as described in FIG. 4B, is labeled using a predetermined set of rules to delineate its physical and physiological properties. The rules may comprise quantitative parameters, in which the ability of a given organ or tissue to be penetrated is represented on a scale, as described in the description of FIG. 4C and FIG. 4D above. The organ is assigned a penetrability value according to a function Ym, where m are parameters relating to factors contributing to tissue traversability in the given organ or tissue. If the organ is penetrable, it is assigned a relative value corresponding to either or both of its absolute penetrability, or its penetrability relative to other tissues along the surgical path. If the organ is regarded as impenetrable because of the danger to life which such a penetration would incur, then the value of Ym is set at ∞, such that a surgical path including this organ would be absolutely forbidden, and the surgical path always avoids this organ completely. Additionally, another factor to be considered in the assessing the effect of the tool path confronting an organ or tissue, is the relative flexibility of the organ or tissue, and a flexibility cost function, Xm is used together with the penetrability cost function (Ym) to calculate the relative traversability values for each organ and tissue. The flexibility cost function may include characteristics such as compressibility, capsule or fascia strength, density, and friability. Additional intrinsic tissue parameters (Zm, etc.) may be used to compute an overall cost function of a specific path, the additional parameters relating to factors contributing to tissue traversability of an individual tissue, such as innervation, essentiality for life, relative risk of moving the tissue, and risk of penetration. In calculating the total cost for a specific path containing tissues or organs labelled n, where n=1, 2, 3, . . . N, the cost function of each tissue or organ along the path, i.e., the weighted tissue penetrability and flexibility values, are summed for each tissue or organ along that path to provide an overall path cost function Cp for the path p:

$$C_p = \Sigma_{n=1}^{N}(X_m + Y_m) \quad (1)$$

where the path contains N separate organ or tissue segments.

In step 604, a preliminary surgical plan is developed; in the exemplary implementation illustrated, the procedure is a spinal fusion, such that the screw positions and sizes, surgical decompression, vertebral alignment adjustments, and vertebral interbody size and position are selected. In step 605, the system identifies all potential entry points for the surgical tool path on the surface of the subject's skin. In some cases, these potential starting points may correspond to standard surgical approaches that are used by surgeons to perform a given surgical procedure; however, the system is not limited by these approaches, and may locate or identify other potential entry points for the surgical tool path.

Using a first identified entry point, in steps 606a a path is planned from this entry point to the surgical target in the spinal column, circumnavigating internal organs 2, 3, and 4 in their natural configurations. This would be the optimum access path for the procedure since it does not involve any interference with any of the organs or tissues en route to the target. However, robotic implementation for such a path would require special semi-flexible arms to achieve the curved path shown, and would preclude direct visualization of the path. In step 606b, the same selected entry point and surgical target as in step 606a are connected by a straight trajectory. A linear path, as shown in step 606b, would be a more conventional procedure, and therefore is the preferred path to be used. However, as shown in this illustration, such a trajectory may traverse internal organs, in this example, organs 2 and 3.

Since a linear path passing through most abdominal organs would be a forbidden path, in step 607, the path in step 606b is shown as being achieved by virtually shifting, moving, or compressing the organs or tissues that lie along the straight path, in this schematic example, organs 2 and 3. Unlike a direct path that would penetrate or traverse organs, a plan involving shifting or compressing these organs, using varying degrees of pressure and force, is allowable for most organs such as sections of the digestive tract, bladder, and other organs of the abdominal peritoneal cavity. For the first entry point, the method then determines the overall cost function Cp of the path in step 607, in accordance with equation (1) above. The converged path may be linear, or may introduce one or more degrees of freedom to accommodate the tool being inserted through the opening along the path. Some tools are not linear, but may have joints or a three dimensional shape. Thus, depending on the tool being inserted through the entry point along the path, the geometry of the path may need to adaptable to a three-dimensional shape. Steps 606a, 606b and 607 are repeated for all possibly useful planned paths between selected potential entry points and the target site. In step 608, an evaluation is made to determine whether paths for all of the potential entry points have been calculated. If not, the system controller returns the planning procedure to step 605 to create additional paths for any additional potential entry points. Although more than one path may be identified for an entry point to the surgical target, the search algorithm described in an exemplary embodiment of the methods generally identifies a single path having the lowest cost function from a given entry point to a given surgical target.

Once all possible surgical paths have been considered, based on each of the potential selected entry points, the method proceeds to step 609, in which the cost function for each potential converged path is calculated. The cost function is based on the rules established and the traversability values of the organs calculated in step 603, according to the predetermined set of rules and quantitative parameters, and the cost functions for the various paths are compared. The system searches for the path having minimal resistance, i.e., the lowest cost function. The potential paths for a given procedure comprise the various entry points for a common surgical target; thus, each path may traverse or circumnavigate some of the same organs, albeit from a different side or angle of approach. In step 610, the potential path with the minimum cost is identified and selected as the path of choice for the given patient and surgical procedure, thus designating a specific surgical approach and deciding on the path to be taken to reach the surgical target.

Once the surgical path has been planned by the robotic system as in FIG. 6, the system assesses if the predicted outcome from this path would provide satisfactory results. In this context, a satisfactory result would comprise at least some of: 1) the ability to provide adequate access to the surgical site, 2) acceptable time of dissection to reach the site, and 3) ability of the patient to tolerate the requirements of the surgical procedure. The ability of the system to make accurate predictions is expected to increase over time, as data are collected and stored in a searchable database. Thus, in the final path selection, the system has the capability of incorporating not only the minimal cost function of a potential path, but also other factors. Such factors comprise, for example, the risk of approaching and potentially penetrating an organ with life-threatening consequences, or the predicted postoperative consequences of a given path on the patient's recovery time or long-term health. In the event that the path with the lowest cost function has high intraoperative risks or undesirable post-operative consequences for the patient, the system may select another path that balances the lowest cost function with other identified factors.

At this point, the system either decides that this approach is not ideal and returns to consider other approaches, or proceeds with creating a preoperative plan for execution by the surgical robotic system under the instructions of the controller. Each step of the method is determined by a combination of decisions determined by a logical analysis of the data and the patient's condition, as presented in further detail in FIGS. 2 and 3 herewithin above. The preoperative plan may be supplemented intraoperatively by images acquired by any number of modalities: optical imaging, ultrasound, fluoroscopic, MRI, or CT. Feedback from these live two-dimensional or three-dimensional images may be provided to the system (FIG. 7) for revision or adjustment of the operative plan in real time.

Figure 7:
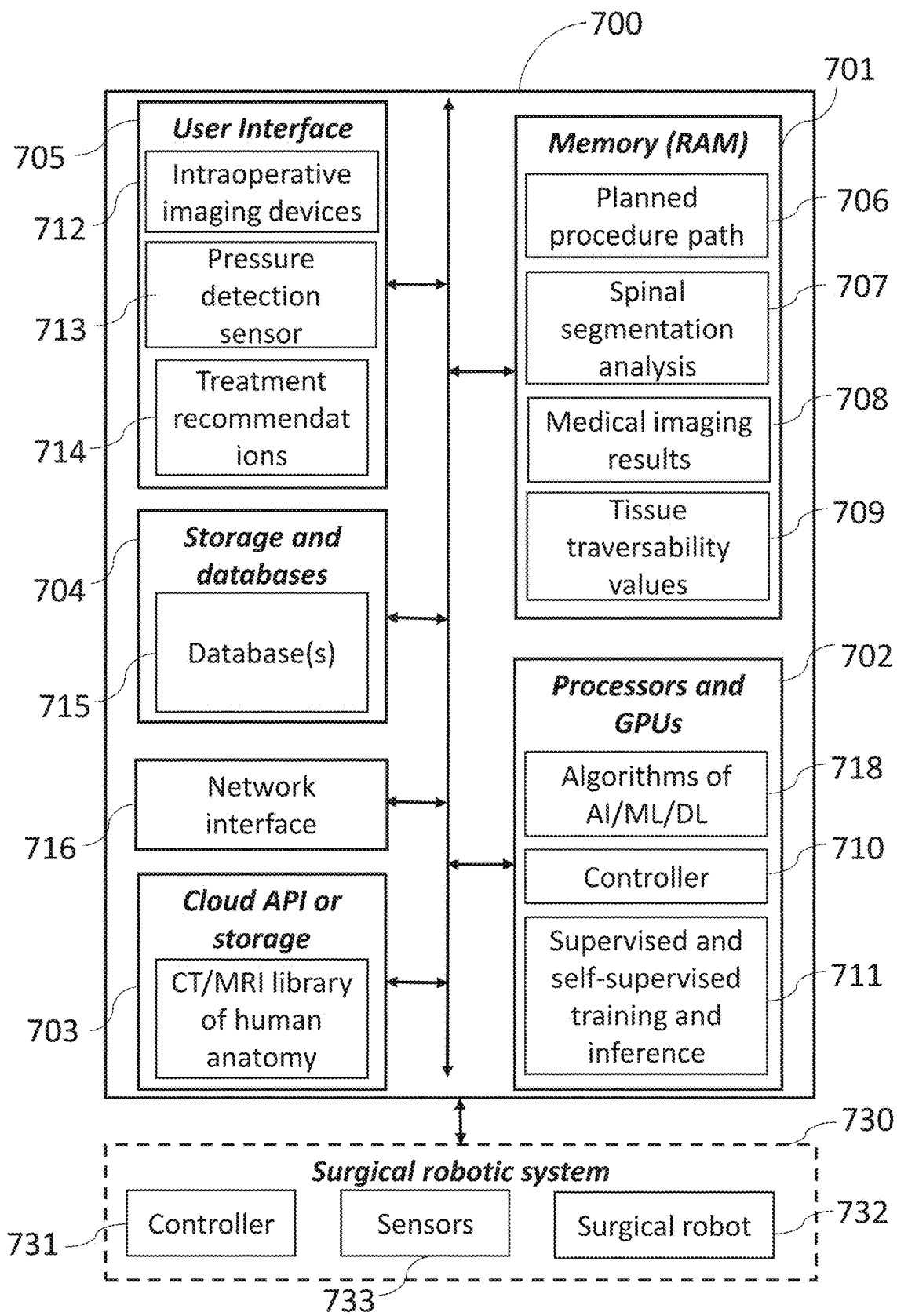
FIG. 7 is a conceptual block diagram that illustrates the structural components that comprise the system used to carry out some implementations of the disclosed methods.

Reference is now made to FIG. 7, schematically showing the components of an exemplary system 700, for implementation of some of the methods described in the present disclosure. The exemplary implementation of the system shown in FIG. 7 comprises a user interface 705, at least one database 704, a cloud application program interface (API) or storage 703 housing an annotated library of CT or MRI images (FIG. 4C), and a network interface 716. The system further comprises a memory (RAM) 601 and at least one processor or graphics processing unit 702. The user interface 705 may comprise an intraoperative imaging interface 712, at least one sensor such as a pressure detection interface 713, and in some implementations, treatment recommendations 714. The storage or database 704 may comprise clinical information regarding past spinal fusion operations (from steps 201, 304).

In a typical operation of one implementation of the system, the RAM component 701 comprises both sources of input for the processing of the method, such as the segmentation analysis 707, tissue traversability values 708, and intraoperative medical imaging results 709. The RAM 701 also stores the output of the method, i.e., the planned procedure path 706, which may be updated intraoperatively based on input from intraoperative imaging 712, pressure detection 713, and other sources of information. The at least one processor and graphics processing unit 702 comprise algorithms of artificial intelligence comprising machine learning and deep learning 718, a controller 710, and optionally training and inference systems 711, which process the inputs derived from other components of the system. The system 700 is configured to communicate with and provide instructions to a robotic surgical system 730, comprised of a controller 731 and surgical robot 732, which carry out the operation according to the system output according to the planned procedure path 706.

During operation of the system, the inputs are stored in the memory 704 or 701, which has several components, comprising: patient clinical data (steps 201, 202), the preoperative MRI or CT images (step 203), the image segmentation (step 302) for tissue boundary analysis that identifies in the preoperative images the edges (step 303) and identity (step 305) of each organ and tissue along the possible access paths to the surgical target. The spinal segmentation analysis 707 is a separate analysis that enables calculation of spinal parameters (step 302), based on the preoperative MRI or CT images. The traversability values 709 for each organ and tissue are stored in the memory as inputs to the system, and used for intraoperative updating of the planned path 706 in combination with the outputs from intraoperative pressure detection via the pressure detection interface 713. These values are derived from one of the databases 704 that has calculated parameters for each tissue type (step 304). These values may be updated based on actual pressure detection measurements taken intraoperatively by a pressure detector mounted on a surgical probe or dilator of the surgical system, and input to the system via the user interface 705. The intraoperative pressure detector 713 provides input on specific organ compressibility, as some patients may have differences in tissue resilience and compressibility depending on age and state of health. For example, a younger person may have stronger muscles than an older person, or a patient with bowel disease may have more fragile intestinal walls.

Another component of the system memory 701 is the intraoperative imaging results 708 that are acquired intraoperatively. These images may comprise fluoroscopic images, ultrasound images, or CT/MRI, and are input to the system via the intraoperative imaging devices 712. The processor 702 integrates all of the various inputs and generates an output comprising a surgical path plan or instructions 606 (FIGS. 5A to 5D), which are provided to the robotic controller 731, to carry out surgical access to the target site. Further components of the system 700 comprise the user interface 605, through which the surgeon or other health care provider interacts with the system. One or more databases 704, comprising data described in steps 201 and 304, are also a part of the system. Data from these databases are used to inform the selection process for planning the optimal path. In some implementations of the disclosed methods, the system 700 provides instructions to a surgical robotic system 730 comprising a controller 731, a surgical robot 732, and at least one sensor 733 for providing feedback regarding tissues along the planned path of the surgical approach to execute the surgical procedure.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The apparatuses and methods described in this disclosure may be partially or fully implemented by one or more computer programs executed by one or more processors. The computer programs include processor-executable instructions that are stored on at least one non-transitory tangible computer readable medium. The computer programs may also include and/or rely on stored data.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure.

What is claimed is:

1. A system for planning a safe path for robotic execution of a surgical procedure on the spine of a subject, comprising:
   at least one processor executing instructions stored on at least one non-transitory storage medium to cause the at least one processor to:
   access a database containing analyses of outcomes of surgical procedures on the spine of patients in a reference population;
   using the outcomes accessed in the database of patients having a similar clinical profile to that of the subject, select the surgical procedure most likely to produce a desired outcome for the subject;
   locate a spinal column at a site of interbody insertion;
   calculate an amount of bone to be removed from the spinal column;
   select a surgical approach from a set of known surgical approaches, the surgical approach expected to be optimal for executing the selected surgical procedure including removing the calculated amount of bone; and
   using a segmented three-dimensional image set annotated with predetermined tissue traversability of tissues in the region of the selected surgical approach, plan paths for robotic access of at least one surgical tool to the spine, for execution of the selected surgical procedure, wherein the optimal planned path is one which minimizes interaction of the at least one surgical tool with tissues having unfavorable traversability data; and at least one interactive user interface to output the amount of bone to be removed and the selected surgical procedure and surgical approach, and wherein the system is configured to calculate and output expected time required from initiation of the procedure to accessing a target by the at least one surgical tool.

2. The system according to claim 1, wherein data of the predetermined tissue traversability data is collected from sources comprising at least some of scientific literature, recordings of tissue properties in prior surgical procedures, and experimental data.

3. The system according to claim 1, wherein the tissue traversability data comprises information on known tissue properties including at least some of density, friability, vascularity, removability, compressibility, essentiality for life, movability, capsule or fascia fragility, or relative risk of penetration.

4. The system according to claim 1, wherein the tissue traversability is assigned a weighting according to a combination of known tissue properties.

5. The system according to claim 4, wherein the weightings of the tissues encountered in a planned path are combined to generate a score for the planned path, such that the planned path with a most favorable score is selected as the optimal planned path.

6. The system according to claim 1, wherein the planned path is selected to achieve at least one of an ability to provide adequate access to the surgical site, a shortest operating time to reach the surgical site, or an ability of the patient to tolerate requirements of the surgical procedure.

7. The system according claim 1, wherein data of the database is classified according to surgical approaches used and the clinical profile of the patients, and wherein the clinical profile comprises at least some of age, gender, BMI, concurrent bone disease, coexisting medical conditions, level of intervertebral disc disease, or clinical risk indices.

8. The system according to claim 1, wherein if intervertebral disc removal is indicated for the selected surgical approach, the surgical procedure on the spinal column comprises one of artificial intervertebral disc replacement or spinal fusion with interbody insertion.

9. A system for robotic execution of a planned procedure path using a preselected surgical approach on a subject, comprising:

at least one processor executing instructions stored on at least one non-transitory storage medium to cause the at least one processor to implement robotic execution of the planned procedure path on the subject;

a memory comprising the planned procedure path, and tissue traversability data that indicate a risk of interacting with each specific tissue along the planned procedure path; and at least one sensor configured to provide an input to the at least one processor to update the tissue traversability data intraoperatively;

wherein the input is used to update the planned procedure path intraoperatively to avoid tissues with unfavorable traversability data, and wherein the system is configured to calculate and output expected time required from initiation of the planned procedure path to accessing a target by at least one surgical tool.

10. The system according to claim 9, wherein the at least one sensor is at least one of an externally situated internal imaging device, a pressure detection sensor, a Doppler flow sensor, an endoscopic camera, a mechanical tonometer, a digital indurometer, a fibrometer, or an ultrasound probe.

11. The system according to claim 9, wherein the tissue traversability data comprise quantitative information on known tissue properties: at least some of density, friability, vascularity, removability, compressibility, essentiality for life, movability, capsule or fascia fragility, or relative risk of penetration.

12. The system according to claim 9, wherein the tissue traversability data comprise a series of numerical ratings for each tissue, wherein each numerical rating corresponds to one of known tissue properties.

13. The system according to claim 9, wherein the processor is configured to use at least one of training logic, inference logic, artificial intelligence algorithms, machine learning, or computer logic to execute the planned procedure path using the preselected surgical approach.

14. The system according to claim 9, wherein the input of the sensor is used to update the planned procedure path intraoperatively in order to enhance at least one of safety or efficiency of the robotic execution.

15. A system for selecting a specific surgical procedure to be performed on a subject having a clinical condition for which intervertebral disc removal is indicated, comprising:

at least one non-transitory storage medium for storing instructions; and at least one processor executing the instructions stored on the at least one non-transitory storage medium, the processor performing:

classify clinical parameters data and surgical outcome data from patients in a reference population, each patient having undergone a surgical procedure for intervertebral disc removal using any one of a set of known surgical approaches;

match clinical parameters of the subject to a subgroup of the reference population having an equivalent clinical condition to that of the subject;

based on the classified surgical outcome data of patients in the matched subgroup, select the specific surgical procedure and a surgical approach predicted to result in an optimal outcome for the subject; and calculate and output an amount of bone to be removed; and at least one interactive user interface to output the amount of bone to be removed and the selected surgical procedure and surgical approach, and wherein the system is configured to calculate and output expected time required from initiation of the procedure to accessing a target by at least one surgical tool.

16. The system according to claim 15, wherein the clinical conditions for which intervertebral disc removal is indicated are at least one of herniated disk, intervertebral disc disease, spinal stenosis related to disc disease, or spondylolisthesis.

17. The system according to claim 15, wherein the clinical data and the surgical outcome data of the reference population are derived from at least one of hospital records, health maintenance organization records, insurance company records, or the records of a surgical practice.

18. The system according to claim 15, wherein the surgical outcome data comprise at least some of time to recovery, extent of recovery, level of independence in activities of daily living, reported level of pain, Oswestry disability index score, range of mobility of an affected vertebral segment, and motor function.

19. The system according to claim 15, wherein the known surgical approaches comprise anterior approach, oblique approach, lateral approach, posterior approach, and transverse approach.

20. The system according to claim 15, wherein the processor assigns the subject to the selected surgical procedure and surgical approach using iterative processing to determine a combination of surgical procedure and surgical approach most likely to result in an optimized outcome for the subject.

* * * * *